Figure 1:
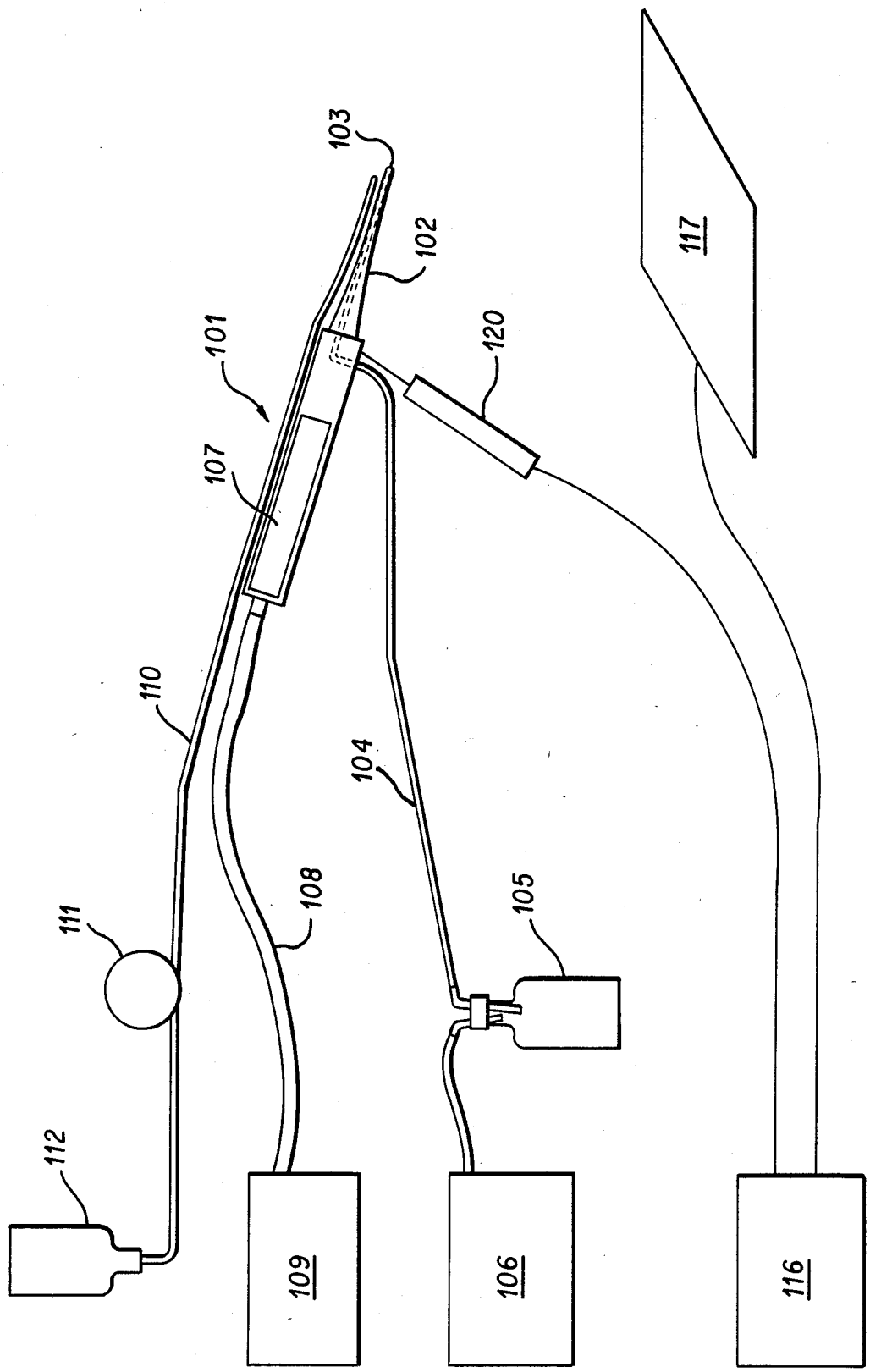

United States Patent [19]

Wiksell

[11] Patent Number: 4,886,060
[45] Date of Patent: Dec. 12, 1989

[54] EQUIPMENT FOR USE IN SURGICAL OPERATIONS TO REMOVE TISSUE

[75] Inventor: Hans Wiksell, Odlingsvägen, Sweden

[73] Assignee: Swedemed AB, Uppsala, Sweden

[21] Appl. No.: 349,966

[22] Filed: May 8, 1989

Related U.S. Application Data

[63] Continuation of Ser. No. 45,927, May 4, 1987, abandoned.

[30] Foreign Application Priority Data

Mar. 20, 1987 [SE] Sweden ................................ 8701153

[51] Int. Cl.⁴ ............................................. A61B 17/36
[52] U.S. Cl. ............................. 128/303.14; 128/24 A; 604/22
[58] Field of Search .............. 128/24 A, 303 R, 303.1, 128/303.14, 303.17, 328; 604/22, 43

[56] References Cited

U.S. PATENT DOCUMENTS

| | | |
|---|---|---|
| 2,514,080 | 7/1950 | Mason . |
| 2,748,298 | 5/1956 | Calosi et al. . |
| 3,447,051 | 5/1969 | Attwood et al. . |
| 3,862,630 | 1/1975 | Balamuth . |
| 4,188,952 | 2/1980 | Loschilor et al. ................ 128/24 A |
| 4,223,676 | 9/1980 | Wuchinich et al. ................... 604/43 |
| 4,271,371 | 6/1981 | Furuichi et al. . |
| 4,371,816 | 2/1983 | Wieser . |
| 4,417,578 | 11/1983 | Banko . |
| 4,425,115 | 1/1984 | Wuchinich . |
| 4,428,748 | 1/1984 | Peyman et al. . |
| 4,445,063 | 4/1984 | Smith . |
| 4,468,581 | 8/1984 | Okada et al. . |
| 4,493,694 | 1/1985 | Wuchinich . |
| 4,515,583 | 5/1985 | Sorich . |
| 4,516,398 | 5/1985 | Wuchinich ........................ 128/24 A |
| 4,526,571 | 6/1985 | Wuchinich ........................ 128/24 A |
| 4,528,979 | 7/1985 | Marchenko et al. . |
| 4,531,934 | 7/1985 | Kossovsky et al. . |
| 4,587,958 | 5/1986 | Noguchi et al. ................... 128/24 A |
| 4,609,368 | 9/1986 | Dotson, Jr. . |
| 4,626,728 | 12/1986 | Flachenecker et al. ............. 310/316 |
| 4,634,420 | 1/1987 | Spinosa et al. ......................... 604/22 |
| 4,674,498 | 6/1987 | Stasz ................................. 128/303.14 |

OTHER PUBLICATIONS

"Ultrasonic Engineering", Julian R. Frederick, pp. 1-130, 1965.
"A Longitudinally Resonant Sub for Vibrations of Large Amplitude", Esiner, et al., *Ultrasonics*, Apr.-Jun. 1965, pp. 88-98.

Primary Examiner—Max Hindenburg
Attorney, Agent, or Firm—Armstrong, Nikaido, Marmelstein, Kubovcik & Murray

[57] ABSTRACT

The present invention relates to an equipment for use in surgical operations to remove tissue, and comprises an ultrasonic knife having a tip intended to be brought into contact with the tissue, a transducer unit causing said tip portion to oscillate longitudinally and a frequency generator to drive the transducer unit, the parts of the ultrasonic knife which are in contact with the patient being galvanically isolated from the other equipment of the knife, as well as means for temporarily supplying thermal energy to the tissue from the tip portion of the ultrasonic knife in order to achieve hemostasis by means of coagulation.

12 Claims, 3 Drawing Sheets

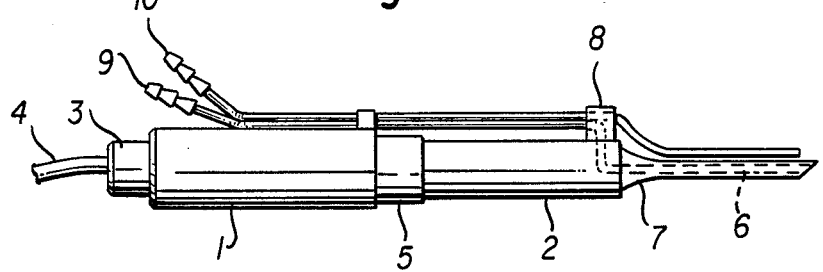
Fig. 2
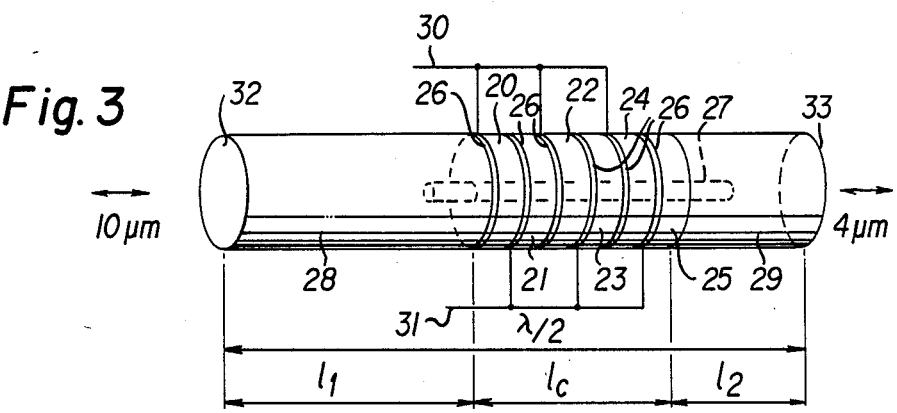
Fig. 3
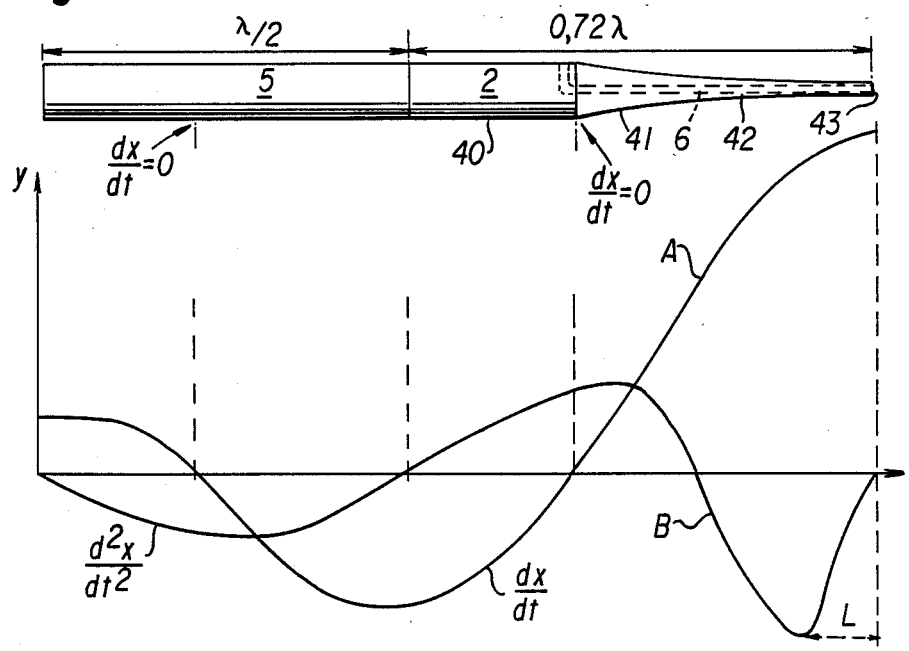
Fig. 4
Fig. 7

EQUIPMENT FOR USE IN SURGICAL OPERATIONS TO REMOVE TISSUE

This application is a continuation of application Ser. No. 045,927 filed May 4, 1987, now abandoned.

The present invention relates to an equipment for use in surgical operations to remove tissue.

Various types of ultrasonic knives are used for surgical operations to remove tissue.

This kind of operation often requires an equipment which can rapidly alternate between cutting and removal of waste tissue, as well as having a coagulation function to stem the frequent bleeding. There is thus a great need for an ultrasonic knife which, besides the knife and aspiration functions described above, also includes a hemostasis function.

Two usual types of dielectric coagulation are routinely used in operations to achieve hemostasis, i.e. bipolar and monopolar coagulation. Special bipolar tweezers are usually used for bipolar coagulation, the two jaws being insulated from each other and designed to permit an RF generator, for instance, to supply RF energy between the jaws. This ensures that bipolar coagulation is carried out with great precision between the tips of the two tweezer jaws and is therefore normally used in surgery requiring great precision, such as brain surgery. For monopolar coagulation an RF generator is used, for instance, which supplies RF voltage between a large indifferent electrode applied on the patient and the tip of a special coagulation hand instrument. The heating obtained through the large area of the indifferent electrode in contact with the patient's skin is negligible. However, strong local heating is obtained at the tip of the hand instrument when applied to a blood vessel, for instance. It is quite usual for a surgeon, instead of directing the tip of the coagulation instrument to the tissue, to allow an assistant to hold this in direct metallic contact with an ordinary pair of tweezers, a scalpel or the like. To obtain this function, the surgeon requests the assistant to "coagulate against the tweezers".

Such an alternative use—i.e. use as either knife or coagulation instrument—has so far not been realized in ultrasonic knives since supplying the high-frequency electric energy necessary for coagulation would immediately disturb the electronic part of the ultrasonic knife, possibly even causing a short-circuit through the protective earthing of the hand instrument.

The present invention has the object of achieving an operation equipment for the above-mentioned purpose, which comprises an ultrasonic knife with unusual functions, i.e. also including a coagulation function.

This is achieved in accordance with the invention by an equipment comprising an ultrasonic knife having a tip intended to be brought into contact with the tissue, a transducer unit causing said tip portion to oscillate longitudinally and a frequency generator to drive the transducer unit, the parts of the ultrasonic knife which are in contact with the patient being galvanically isolated from the other equipment of the knife, as well as means for temporarily supplying high-frequency energy to the tissue from the tip portion of the ultrasonic knife in order to achieve hemostasis by means of coagulation.

The tip portion of the ultrasonic knife is suitably provided with a central duct and said tip portion of the ultrasonic knife is arranged to cooperate with a duct for the supply of liquid, preferably a saline solution.

According to a preferred embodiment of the invention, the coagulation unit suitably comprises means for emitting high-frequency electrical energy which induces heat in the tissue.

Other features of the invention are revealed in the following claims.

Figure 5:
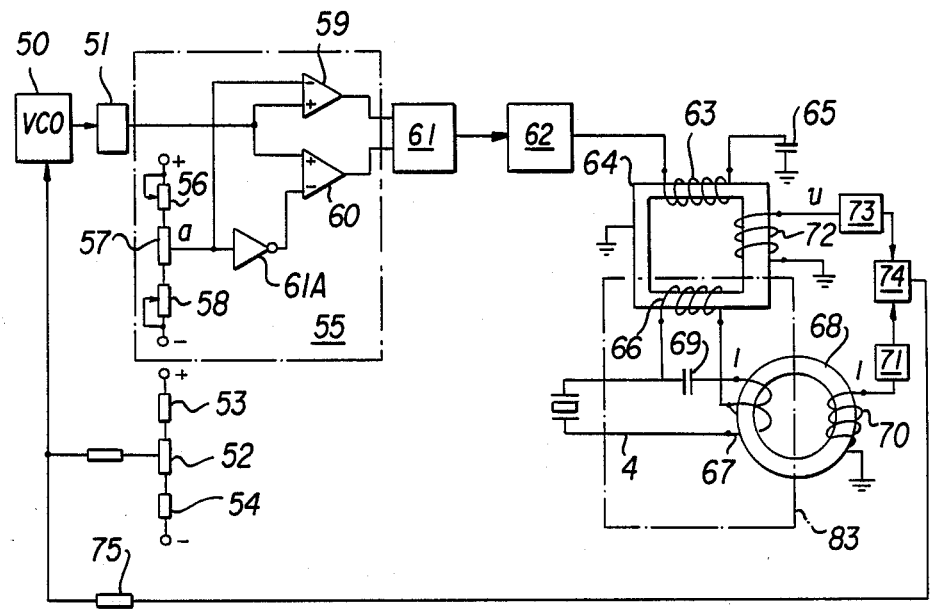
Figure 6:
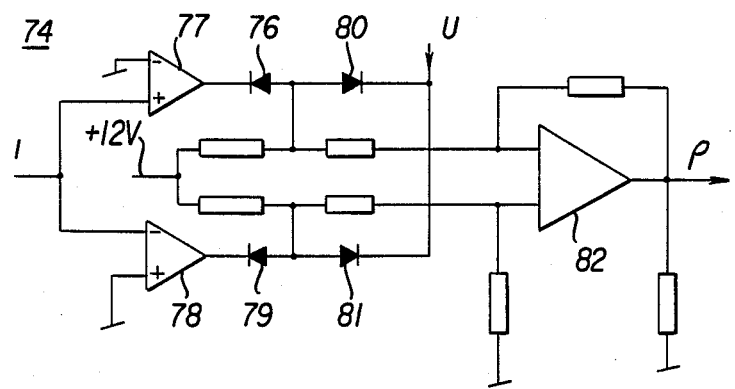

The invention will now be described in detail with reference to a number of embodiments shown in the accompanying drawings in which FIG. 1 shows in principle a first embodiment of an equipment according to the invention, FIG. 2 shows a side view of an ultrasonic knife particularly suitable for the device according to the invention, FIG. 3 illustrates the transducer unit in the knife according to FIG. 2, FIG. 4 illustrates the amplitude transformer for the knife according to FIG. 2, FIG. 5 is a block diagram of the equipment for supplying electricity to the knife according to FIG. 2, FIG. 6 is a detailed block diagram of the phase comparator according to FIG. 2, and FIG. 7 is a diagram illustrating the amplitude distribution along the amplitude transformer according to FIG. 4.

In the embodiment of the invention illustrated in FIG. 1, the handle of an ultrasonic knife is designated 101. Attached to the handle 101 is a tapering knife portion 102 with a central duct 103. This duct 103 communicates via a tube 104 and a suction bottle 105, with a vacuum pump 106 and is designed to remove tissue, etc.

The handle 101 also includes a transducer unit 107, connected by leads 108 to a frequency generator 109. The handle also includes a tubular connection 110 which is connected via a pump 111 to a container 112 for irrigation liquid. The equipment also includes a coagulation unit, an RF generator 116 which, in order to achieve a high-frequency voltage for monopolar coagulation, is connected both to the tip portion 102 of the knife and to an indifferent electrode 117 placed against the patient's body in the form of a metal foil, for instance.

The device shown in FIG. 1 complies with modern requirements for electrical safety with what is known as cardiac floating isolation. This means that the electrical parts of the equipment, comprising the outer casing are earthed and the handle itself is electrically insulated from earth. The leakage current is thus so low that protection class IEC 601-1 is fulfilled.

As previously mentioned, it is of great interest to expand the method described above to enable it to be used for the handle for the ultrasonic knife as well. It should be noted that the frequency used for monopolar coagulation is generally in the range 0.5–30 MHz and that the unloaded RF voltage can reach extremely high values (1000 V). The use of cardiac floating isolation for the ultrasonic aspirator obviously enables monopolar coagulation to be performed with the handle of the ultrasonic aspirator as a completely passive conductor, just as if it were a pair of tweezers. However, it must be pointed out that this method entails extremely high strain on the insulation circuit of the ultrasonic aspirator. This insulation circuit must be specially dimensioned to withstand the RF energy to earth without the risk of resonance phenomena, for instance, in the winding of the isolation transformer, which might result in resonance phenomena with standing waves leading to high voltages and/or currents locally in the winding and its insulation. These might in turn result in extreme heating in the isolation unit in the frame. However, we have deemed the advantages of being able to cut, remove tissue and coagulate with one and the same hand instrument to be so great that, despite this, we dimensioned the handle of the aspirator to enable it to be used for monopolar coagulation. The advantage of a saline-solution drip possible with the equipment is thus obvious. The slow supply of saline solution during monopolar coagulation has several advantages, such as cooling of the surrounding tissue and a more gentle and better controlled heating process. (Saline-solution drips are often used for ordinary diathermic coagulation.) When the surgeon wishes to effect coagulation with the handle of the ultrasonic knife he can merely request his assistant to hold the point of the electro-coagulator against some naked metal part on the handle of the ultrasonic knife, exactly as if the latter were a pair of tweezers.

According to a further development of the invention, circuits are also inserted in the frame of the ultrasonic device to permit retention of the superposition principle even during coagulation, for the phase-locking functions necessary for the ultrasonic function. An ultrasonic knife has such a narrow band width that the feeding oscillator must be phase-locked to ensure stable accoustic output irrespective of variations in resonance frequency for the handle which appear due to varying temperature and variations in the amount of tissue blocking the central duct in the tip portion. For the ultrasonic knife according to the invention, the variations reach 0.5% of the ultrasonic frequency and these 0.5% variations must be accurately reproduced by the electronics of the frame in order to ensure good ultrasonic stability. If this is to occur in the ultrasonic knife, therefore, the phase angle between current and voltage must be measured for the ultrasonic energy supplied to the handle and this phase angle must then be converted to a control signal which is returned to the oscillator, phase-locking this to follow the required resonance-frequency variations. These measures to retain the superposition principle enable the ultrasonic aspirator to operate with both ultra-sound and RF energy in parallel, without interaction. For certain operations this has been found to have extremely synergetic effect since the ultrasonic dissection can be effected simultaneously with suitable dielectric coagulation, thus enabling work to progress more quickly and with less bleeding. Furthermore, tissue has less tendency to adhere to the tip—a feature characteristic of monopolar methods—due to the high acceleration forces arising with ultra-sound (up to 340,000 times earth acceleration).

The ultrasonic knife shown in FIGS. 2-7 can advantageously be utilized in the device proposed according to the invention. The invention is of course not limited to use of this particular knife, although in many respects it has certain advantages.

The ultrasonic knife shown in FIGS. 2 to 7 comprises a handle 1, a knife 2, a connection 3 for a two-wire connection supplying alternating voltage at ultrasonic frequency to a transducer unit 5, to which the handle 1 is attached. The transducer converts this alternating voltage to a linear oscillating movement, which is transmitted to the knife 2 functioning as an amplitude transformer, the geometry of which is described in detail below.

A bore 6 extends centrally through the tip 7 of the knife and is deflected radially outwards at a schematically illustrated connection 8 for an aspiration tube 9.

There is also a tube 10 for supplying isoton saline solution to the knife tip. As mentioned in the introduction, it is important that the free end of the knife tip executes a purely longitudinal oscillating movement without any suggestion of transverse oscillation components.

The transducer in FIG. 2 includes six rings 20–25 of a sintered ceramic material (lead titanate zirconate) between which there are inserted holed discs 26 of copper-berylium alloy. The rings 20–25 and discs 26 are placed on a titanium pin 27 threaded at both ends. There is an unillustrated sheath of electrically insulating material, teflon, thrust on to the pin to serve as electrical insulation for the discs 26. Cylindrical resonance rods 28, 29 made from the magnesium alloy or dyralumin are each threaded on to the respective end of the pin 27, and the whole unit 20–29 is tightened into a pack so that the rings 20–25 are statically prestressed such as to give a pressure of about 500 kg/cm$^2$, in order to withstand without this disintegration the heavy accelerations to which they are subjected when the feed voltages from the two-wire cable 4 are put across the lines 30, 31, which are electrically connected to the discs 26 such that one line is connected to alternate discs while the other line is connected to the remaining discs.

The transducer has a length which is half the wave length of the alternating current with which it is fed. The length of the resonator rods 28, 29 are different and are determined by the following relationship:

$$\frac{\omega_c l}{v_c} + \tan^{-1}\left[\left[\frac{A_1 \cdot P_1 \cdot v_1}{A_c \cdot P_c \cdot v_c}\right] \cdot \tan\left[\frac{\omega_1 l}{v_1}\right]\right] +$$
$$+ \tan^{-1}\left[\left[\frac{A_2 \cdot P_2 \cdot v_2}{A_c \cdot P_c \cdot v_c}\right] \cdot \tan\left[\frac{\omega_2 l}{v_2}\right]\right] = \pi$$

where $f = \frac{\omega}{2\pi}$ and where $l_1$, $l_2$, $l_c$ denote the length of the rod 28, 29, the length of the aggregate of the rings 20, 25 respectively; $v_1$, $v_2$, $v_c$ denote the velocity of sound for the same units; $A_1$, $A_2$, $A_c$ denote the cross-sectional area of these units; $P_1$, $P_2$, $P_c$ denote the density of these units. According to an advantageous embodiment of the invention the relationship $l_1: l_2 = 2.5$, the transducer then oscillating with a stroke of about 10$\mu$m at the end surface 32 and with 4$\mu$m at the end surface 33. The amplitude transformer is connected to the end surface 32 of the transducer and amplifies the magnitude of the stroke by about 30 times.

The transducer and the amplitude transformer are united by means of a bolt which connects the two units together with an ample degree of coupling.

The inventive amplitude transformer has a length in the order of magnitude 0.72 times the wavelength of the ultra sound, and is made in a cohesive piece from a material which is a heat-treated titanium alloy including aluminium and vanadium. The iron content may be at most 0.3% and the hydrogen content at most 0.01%. The amplitude transformer includes three sections 40, 41, 42. Section 40 has a cylindrical form and merges into section 41, the geometry of which is a wave function of the fourth order Fourier form i.e.

$$U(X) = \sum_{n=0}^{n=3} a_K \cdot \cos K \cdot \pi \cdot X$$

where

U(X)=longitudinal deflection in X-direction $a_K$=constants

The section 42 is substantially tapering. With this embodiment of the knife there is obtained a pronounced resonance related to the longitudinal oscillation movement, and from the frequency aspect, this resonance is greatly separated from secondary longitudinal resonances and remaining resonances related to transverse oscillations. As will be seen from the diagram in FIG. 7, read in conjunction with FIG. 4, where the abscissa relates to the length of the amplitude transformer in respect of curves A and B, and the ordinate relates to the longitudinal oscillation in respect of curve A and the magnitude of material stress in respect of curve B, it will be seen that the stroke of the knife is at a maximum at the outmost tip 43 and decreases towards zero at the point where the bore 6 opens out in the surface. It is thus possible to seal the connection of of the suction tube to the bore with 0-ring seals, which will when not disintegrate due to vibration. For the same reason, the handle 1 is attached to the transducer 5 at a velocity node, whereby the handle will not vibrate and the surgeon'hand will not be inured by vibrations. Furthermore, it will be seen from the curve B that material stresses are at a maximum, not at the outmost tip 43 but in a region situated a distance L inwards of this tip. The advantage of this geometry of the knife is that its life increases substantially in comparison with known knives.

It is easy experimentially to check where the resonances of the knife are by connecting it to the transducer and feeding the latter with electrical energy at ultrasonic frequency, adjusted to different frequencies. The stroke executed by the outmost tip 43 is measured by a dial gage, and the crests in the curve obtained from these measurements denote the different resonance points of the knife.

FIG. 5 is a block diagram of the power supply and frequency control of the ultrasonic knife. A voltagecontrolled oscillator 50 sends a square wave voltage with an ultrasonic frequency to an integrator 51. The frequency range of the voltage-controlled oscillator is adjusted with a dc voltage taken from a voltage divider 52, 53, 54 comprising a frequency adjusting potentiometer 52. By the integrator 51 the square wave voltage is converted into a triangular wave from which is supplied to a power adjustment device 55 where it is compared with a constant, adjustable, dc voltage level taken from a further voltage divider 56, 57, 58 via a power adjustment potentiometer 57. The maximum and the minimum power respectively are set by potentiometers 56, 57. The power adjustment device 55 comprises two voltage comparators 59, 60, embodied by two differential amplifiers, as well as an inverter 61A. The power adjustment device 55 operates in the following manner; with the potentiometer 57 the surgeon sets the desired rate of tissue removal within the extreme values which typically range from about 5 $\mu$m to about 300 $\mu$m. Normally the ultrasonic knife is operated with 50–15 $\mu$m. At a the voltage corresponds to the desired power level. This power level reference voltage is supplied to the inverting input of comparator 59 and via inverter 61A in opposite phase to the inverting input of comparator 60. The triangular wave voltage from integrator 51 is compared with said power level reference voltage. The differential amplifiers will change their output states each time the triangular wave voltage crosses the power level reference voltage. The output signals from comparators 59 and 60 are combined in a pulse width filter 61 from which the combined pulse width modulated signal is supplied to a switched power amplifier 62. Thus, the power amplifier 62 receives a pulse width modulated square wave signal the repetition frequency of which equals that of the triangular voltage wave signal. The width of the pulses, that is the energy contents of the pulses, correspond to the surgeon's demand. The power adjustment is accurate and does not affect the frequency of the ultrasonic power applied to the ultrasonic knife. Short switching times are achieved. Accordingly, power control is performed without varying the supply voltage.

From the power amplifier 61 the amplified square wave signal is fed to a primary winding 63 on a ring core transformer 64, the core of which is earthed. The other end of the primary winding 63 is earthed via a capacitor 65. The power-amplified square wave voltage is transformed up in the ring transformer and is taken out across the secondary winding 66 of the transformer where it is fed via a primary winding 67 of a current transformer 68 to the two-wire cord 4. More specifically, one of the cord wires is connected to one end of the secondary winding 66 and to one plate of a capacitor 69 the other plate of which is connected to one end of the primary winding 67 on the current transformer 68. The other end of this primary winding 67 is connected to the other wire of the two-wire cord and the center tap of the current transformer is connected to the remaining end of the secondary winding 66 on the ring transformer 64. The current transformer 68 has a secondary winding 70, one end of which is earthed and the other end of which is connected to an amplifier 71. The ring transformer 64 also has secondary winding 72, one end of which is earthed and the other end connected to the input of an amplifier 73. It is obvious that the voltage U through the secondary winding 72 is proportional to the square wave voltage fed to the knife, while the current I in the secondary winding 70 is proportional to the magnitude of the current with which the knife is fed. The phase position between the supply voltage current and voltage is detected in a phase detector 74 having on its output a direct voltage proportional to the phase difference. This direct voltage is fed to the control input of the voltage controlled oscillator 50 via a resistor 75. It is suitable to arrange so that the phase angle is zero when the ultrasonic knife has a resonance at the mentioned fundamental frequency. This is arranged by the secondary winding 66 of the transformer being dimensioned such that it satisfies the equation:

$$L^2 = f^2 \cdot \pi^2 \cdot C_o^{-1}$$

where L denotes the inductance in H of the secondary winding 66, f is the frequency of the square wave voltage and $C_o$ the capacitance across the ultrasonic knife including the two-wire cord 4. If this equation is satisfied, the ultrasonic knife and its cord behave as a pure ohmic load at the desired resonance frequency.

The capacitor 69 compensates the capacitance of the twowire cord 4. This cord capacitance is great when the cord is long, and with the aid of the capacitor 69 it is achieved that the cord capacity does not affect the phase angle of the ultrasonic knife. The network with the components 66–69 also has the effect that it provides a phase shift enabling the capacitor 69 to be used as compensator for the capacitance of the two-wire cable 4.

The phase error magnitude is dependent on the degree of filling of the duct 6, i.e. the amount of fragments and liquid in the duct 6, causing the oscillating system to be modified and its resonance frequency to change. It is then necessary for the frequency generator immediately to send a feed voltage with the new resonance frequency, otherwise the knife would stop its removal of tissue material. The error signal from the phase detector 74 adjusts the voltage controlled oscillator 50 to the new resonance frequency of the knife. It is now important that the phase detector does not lock on to a spurious resonance frequency during this regulation process. However, since the knife has a geometry stated, these undesired frequencies are greatly separated from the desired resonance frequency. This means that filters and the like can be excluded fom the phase control circuit. A simple detector of the kind illustrated in FIG. 5 may be used instead. The signals U and I are each fed to the respective diagonal branch of the bridge-connected detector 74 which has a diode 76, an amplifier 77, a second amplifier 78 and a diode 79 in one branch and in its other branch a diode 80 and a second diode 81. The voltage between the branches of the bridge is detected by the amplifier 82, sending on its output the mentioned direct current signal, the level of which corresponds to the phase angle between current and voltage for the power fed to the ultrasonic knife.

Apart from the above-mentioned advantage with automatic phase control, the phase lock means that if the operator accidentally drops the knife on the floor, for example, he only need to take a new knife and connect it to the two-wire cord and continue the operation, without having to carry out any calibrations of the electrical equipment. This is an advantage in comparison with the US-A-4 223 676, where renewed calibration of the frequency control must be carried out if the tip is changed.

The ring transformer secondary winding 66, the current transformer primary winding 67 and the capacitor 69 are built into a housing, schematically indicated by the dashed line 83 in FIG. 5, this housing being mechanically connected to the casing of the frequency generator. The housing 83 serves as a screen and surrounds the circuits which are in galvanic communication with the patient. In this way there is achieved that leakage voltages to the supply and other components can be kept so low that the frequency generator meets the protective standard IEC 601-1, class body floating.

For the clinically tried ultrasonic frequency 24000 Hz an amplitude transformer in accordance with the invention has its desired resonance frequency at 24500 Hz. There is a weak transverse resonance at 20200 Hz and a weak, probably transverse resonance at 30200 Hz. It will thus be understood that with this geometry the undesired spurious resonances are at a frequency range from 17% to 23% from the desired frequency, i.e. about 20% with reference to the desired resonance frequency.

The resonance frequency for the ultrasonic transformer varies by only about 120 Hz during operation of the ultrasonic aspirator which means that the control input to the voltage controlled oscillator 50 can have the simple implementation illustrated to the left in FIG. 4 and which comprises a voltage divider 52-54, having an output voltage adjustable to the desired voltage level with the aid of a potentiometer 52. This voltage level thus biases the voltage controlled oscillator to the desired resonance frequency.

The ultrasonic knife unit can suitably be combined with a device for supplying liquid, preferably in the form of a saline solution. This enables a certain cooling effect to be achieved in the operation area, which is important in many cases to prevent damage to surrounding tissues.

The invention is of course not limited to the embodiments shown in the drawings, but can be varied in many ways within the scope of the following claims. Furthermore, as already mentioned, many types of ultrasonic knives can be used, other than the embodiment described with reference to FIGS. 2-7.

I claim:

1. An apparatus for use in surgical operations to remove tissue, comprising an ultrasonic knife means having a contact tip portion for contacting and imparting ultrasonic energy to the tissue to thereby impart ultrasonic vibrations and shattering forces to the contacted tissue so as to cut the tissue, transducer means which operates at ultrasonic frequency for ultrasonically oscillating the tip portion longitudinally and an ultrasonic frequency generator coupled to the transducer means for driving the transducer means, wherein the elements of the ultrasonic knife means in contact with the patient are electrically isolated from the other elements of the knife means, and coagulation means for temporarily emitting high-frequency energy for inducing heat in the tissue from the tip portion of the ultrasonic knife means for coagulating the tissue in order to achieve hemostasis.

2. An apparatus as claimed in claim 1, wherein the tip portion of the ultrasonic knife includes a central duct.

3. An apparatus as claimed in claim 1, wherein the coagulation means includes means for emitting high-frequency electrical energy which induces heat in the tissue.

4. An apparatus as claimed in claim 1, wherein the transducer means is an elongate integral unit having a substantially cylindrical portion, an intermediate portion and a tapering tip portion with a through bore for aspirating comminuted tissue, the length of the transducer being in the order of magnitude 0.72 times the wavelength of the ultrasonic frequency, the intermediate portion having a geometric form corresponding to the fourth order Fourier curve and the tip portion being conical.

5. An apparatus as claimed in claim 1, wherein the transducer is made from a heat-treated alloy of titanium, aluminum, vanadium and iron with a hydrogen content of less than 0.3% and an oxygen content of less than 0.01%.

6. An apparatus as claimed in claim 1, including a voltage-controlled oscillator, a power amplifier connected to the oscillator and a control loop for the frequency control of the oscillator in response to the magnitude of a phase error between the current (I) and the voltage (U) of the energy the power amplifier feeds to the ultrasonic knife.

7. An apparatus as claimed in claim 6, wherein the control loop comprises a ring core transformer having primary and secondary windings for the feed energy, a winding positioned on the ring core transformer for sensing the voltage (U) of the feed energy, a current transformer for sensing the current (I) of the feed energy and a phase comparator for sensing the phase difference between said current and voltage and for feeding a direct voltage signal corresponding thereto to the control input of the oscillator.

8. An apparatus as claimed in claim 7, wherein the current transformer has a primary winding provided with a central tap, the tap being connected to one end of the secondary winding of the ring core transformer, one end of the primary winding being connected to one plate of a compensation capacitor and the other end being connected to one wire of a two-wire cord connecting the ultrasonic knife to the frequency generator, the second plate of the compensation capacitor being connected to the other wire of the core, the other wire being connected to the other end of the secondary winding of the ring transformer.

9. An apparatus as claimed in claim 7, wherein the capacitance of the compensation capacitor is selected such that it compensates for the cable capacity of the two-wire cord.

10. An apparatus as claimed in any one of claims 7–9, wherein the secondary winding of the ring core transformer is dimensioned to satisfy the equations:

$$L^2 = f^2 \cdot \pi^2 \cdot C_o^{-1}$$

where
L = the inductance (H) of the secondary winding
f = the frequency (Hz) of the feed energy
$C_o$ = the capacitance of the ultrasonic knife
the phase difference between I and U being zero degrees at the desired resonance frequency.

11. An apparatus as claimed in any one of claims 7–9, wherein the secondary winding of the ring core transformer, the primary winding of the current transformer and the compensation capacitor are positioned in a screen housing which is mechanically attached to the frequency generator chassis.

12. An apparatus as claimed in claim 1, including duct means positioned adjacent the tip portion for supplying liquid to the vicinity of the tip portion.

* * * * *